United States Patent [19]

Matsuda et al.

[11] Patent Number: 4,624,756

[45] Date of Patent: Nov. 25, 1986

[54] METHOD FOR PRODUCTION OF ORGANIC ELECTROCONDUCTIVE CRYSTALS

[75] Inventors: Hiro Matsuda; Hachiro Nakanishi; Masao Kato, all of Ibaraki; Yuji Orihashi, Hino; Norihisa Kobayashi; Eishun Tsuchida, both of Tokyo, all of Japan

[73] Assignees: Agency of Industrial Science and Technology; Ministry of International Trade and Industry, both of Tokyo, Japan

[21] Appl. No.: 831,502

[22] Filed: Feb. 21, 1986

[30] Foreign Application Priority Data

Mar. 4, 1985 [JP]  Japan ................................. 60-42491

[51] Int. Cl.$^4$ ............................................... C25C 3/00
[52] U.S. Cl. ............................ 204/59 R; 204/59 QM; 540/141
[58] Field of Search ................. 260/245.87; 204/59 R, 204/59 QM

[56] References Cited

U.S. PATENT DOCUMENTS

| | | | |
|---|---|---|---|
| 3,672,979 | 6/1972 | Gerace et al. | 260/245.87 |
| 4,031,109 | 6/1977 | Griffiths | 260/245.87 |
| 4,563,300 | 1/1986 | Marks | 252/500 |
| 4,563,301 | 1/1986 | Marks et al. | 252/500 |

FOREIGN PATENT DOCUMENTS 3245750  6/1984  Fed. Rep. of Germany .

OTHER PUBLICATIONS

Metz et al., J. Am. Chem. Soc. 1983 (105) pp. 828–830.
Orihashi et al., Chem. Lett. 1985, pp. 1617–1620.

*Primary Examiner*—Arthur P. Demers
*Attorney, Agent, or Firm*—Oblon, Fisher, Spivak, McClelland & Maier

[57] ABSTRACT

Cyanometallophthalocyanine crystals which are organic electroconductive crystals are produced by electrolysis of an electrolyte containing an alkali salt of dicyanometallophthalocyanine. Organic electroconductive crystals of better quality are produced by causing the cyanometallophthalocyanine crystals mentioned above to incorporate therein an electron accepting compound and an electron donating compound as doping substances.

6 Claims, 4 Drawing Figures

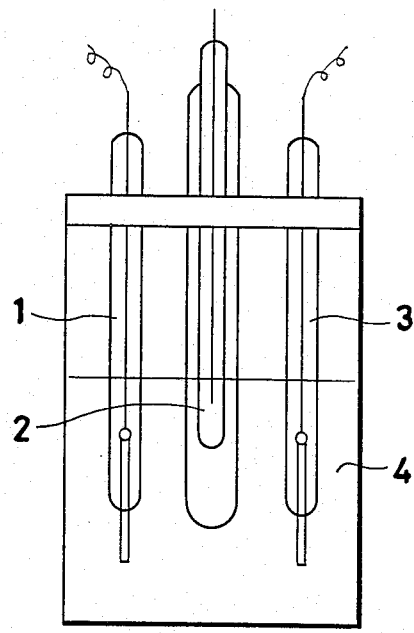
FIG_1
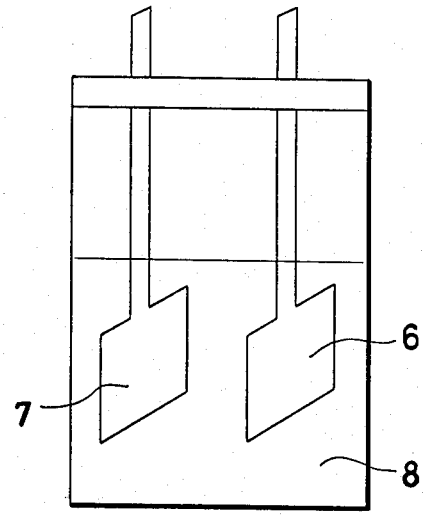
FIG_3
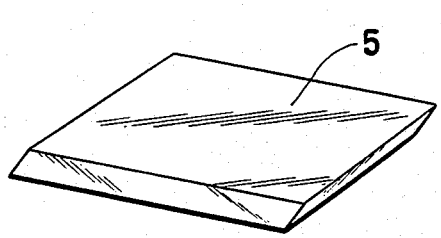
FIG_2
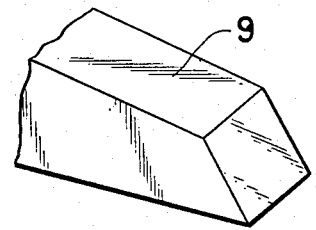
FIG_4

METHOD FOR PRODUCTION OF ORGANIC ELECTROCONDUCTIVE CRYSTALS

FIELD OF THE INVENTION AND RELATED ART STATEMENT

This invention relates to a method for producing novel organic electroconductive crystals by a simple procedure. To be more specific, this invention relates to a method for producing cyanometallophthalocyanine crystals by electrolyzing an electrolytic solution containing an alkali salt of dicyanometallophthalocyanine and to a method for producing cyanometallophthalocyanine crystals doped with an electron accepting compound or an electron donating compound by doping the cyanometallophthalocyanine crystals obtained by the first method with the electron accepting compound or the electron donating compound. The substances produced by these methods of this invention are both organic crystals of high electroconductivity.

The electronics industry is constantly in search of novel and improved materials for the production of component parts, while the material manufacturing industry feels a need for new electroconductive materials of better quality than existing ones. In recent years, the remarkable technical progress in the electronics field has stimulated development of materials suitable for varying purposes. Among such materials, electroconductive materials formed preponderantly of organic substances which excel in workability, mechanical properties, physical properties including density, and chemical resistance are attracting mounting attention for their potential utility in application to electrodes, sensors, photoelectric conversion devices, batteries, semiconductor devices, and even wiring materials.

As organic electroconductive materials, the materials which are formed by adding a doping agent to at least one conjugate high molecular compound such as polyacetylene, poly-p-phenylene, polyphenylene sulfide, polypyrrole have been heretofore known in the art. Although they exhibit varying degrees of electroconductivity falling on the order of $10^{-1}$ to $10^3$ S/cm, they are deficient in stability and are not fully fit for actual use.

Organometallic polymers are also being developed as electroconductive materials. For example, poly(yne) polymers, i.e. polymers containing such metals as platinum, palladium, and nickel, polyferrocenylene containing iron, and polymers having a phthalocyanine of a macrocyclic metal complex bound with a core metal have been proposed. However these do not have sufficient electroconductivity. Among other organometallic polymers, phthalocyanine complexes possess noteworthy chemical stability and are expected to be given improved semiconductor properties and enhanced electroconductivity. Various studies are being made in search of means capable of attaining such improvements. For example, M. Hanack et al. have published a report to the effect that cyanocobalt(III)phthalocyanine is produced when the sodium salt of dicyanocobalt(III)phthalocyanine is extracted with water in a Soxhlet extractor for three days and that the electroconductivity of this extract is $2 \times 10^{-2}$ S/cm (J. Am. Chem. Soc., 105, 828 (1983)). Since the cyanocobalt(III)phthalocyanine so produced is in a powdery form, it is not suitable as a raw material for electronics parts.

In the circumstance, the desirability of developing a material which retains characteristic features inherent in organic materials, possesses sufficient electroconductivity, and is suitable for electronics components has been finding growing recognition.

OBJECT AND SUMMARY OF THE INVENTION

An object of this invention is to provide an organic electroconductive material which is practical, stable, highly shapable highly electroconductive, and suitable for component parts particularly in the electronics industry.

The inventors made a study to realize this object. They have consequently found that large crystals of cyanometallophthalocyanine retaining lasting stability even in the air and possessing high electroconductivity are obtained by electrolyzing a solution containing the alkali salt of dicyanometallophthalocyanine and that these crystals have their electroconductivity further enhanced when they are given a doping treatment. The present invention has been perfected on the basis of this discovery.

BRIEF DESCRIPTION OF THE DRAWINGS

FIG. 1 is a schematic diagram of an electrolytic cell provided with a tripolar electrode and used in Example 1.

FIG. 2 is a diagram illustrating the shape of a crystal produced by the procedure of Example 1.

FIG. 3 is a schematic diagram of an electrolytic cell provided with a bipolar electrode and used in Example 2.

FIG. 4 is a diagram illustrating the shape of a crystal produced by the procedure of Example 2.

DETAILED DESCRIPTION OF THE PREFERRED EMBODIMENTS

This invention aims to provide a method for producing organic electroconductive crystals, which is characterized by the steps of preparing a solution containing an alkali salt of dicyanometallophthalocyanine as an electrolyte and electrolyzing this solution thereby causing deposition of cyanometallophthalocyanine crystals. The present invention further aims to provide a method for producing organic electroconductive crystals, which is characterized by doping the cyanometallophthalocyanine crystals obtained as described above with at least one substance selected from the group consisting of electron accepting compounds and electron donating compounds.

The alkali salt of dicyanometallophthalocyanine to be used in the method of this invention is a cyanophthalocyanine complex having a trivalent metal ion as the core metal thereof and forming a salt with an alkali metal ion such as lithium ion, sodium ion, or potassium ion. Typical examples of the alkali salt are potassium salt of dicyanocobalt(III)phthalocyanine, sodium salt of dicyanocobalt(III)phthalocyanine, potassium salt of dicyanomanganese(III)phthalocyanine, sodium salt of dicyanomanganese(III)phthalocyanine, sodium salt of dicyanoiron(III)phthalocyanine, and potassium salt of dicyanoiron(III)phthalocyanine. It goes without saying that phthalocyanine complexes having such trivalent metal ions as vanadium, niobium, molybdenum, technetium, ruthenium, tantalum, tungsten, rhenium, osmium, and iridium besides cobalt, manganese, and iron as core metal ions are similarly usable. These complexes may be used either singly or in the form of a mixture of two or more freely selected members.

Desirable examples of the solvent for the electrolyte used in the electrolysis include polar nonaqueous solvents such as acetone, acetonitrile, dimethylformamide, and dimethylacetamide. They may be used either singly or in the form of a mixture of two or more freely selected members. The solvent may contain water on the order of several percent.

The alkali salt of dicyanometallophthalocyanine is dissolved in the solvent to prepare an electrolyte. Although the concentration of dicyanometallophthalocyanine in this electrolyte is not particularly limited, it heavily affects the magnitude of electric current used for the electrolysis and, therefore, is desired to fall roughly in the range of 0.1 to 100 m.moles/liter. Generally in the electrolysis of an organic compound, passage of electric current through the electrolytic solution is improved by addition of a supporting electrolyte to the solution. In the method of this invention, the electrolysis proceeds smoothly without requiring such addition of a supporting electrolyte because the alkali salt of phthalocyanine itself is capable of causing ionic dissociation.

These properties required of the electrode used in the method of this invention are only that it not be dissolved under the conditions of the electrolysis involved and that it possess good electroconductivity. Concrete examples of materials for the electrode which meet this requirement are noble metals such as platinum, gold, and palladium and NESA glass. The electrodes can be in the form of a plate, a wire, or a net, for example. Structurally, they can be in a bipolar type consisting of an anode and a cathode or in a tripolar type consisting of the two electrodes just mentioned plus a reference electrode such as a silver-silver chloride electrode. The electrolytic cell is not particularly subject to any restriction except for the requirement that it should be capable of holding therein the aforementioned electrolyte and of enabling the electrodes to be separated by a fixed distance from each other.

In the method of this invention, the electrolysis is desired to be carried out in the form of fixed-potential electrolysis using a bath voltage in the range of 0.8 to 5 V where the electrodes are of the bipolar type or in the form of fixed-potential electrolysis using an anode potential relative to the reference electrode in the range of +0.7 to 2.0 V where the electrodes are of the tripolar type. In this case, the magnitude of electric current is not specifically limited. To ensure production of large defect free crystals of cyanometallophthalocyanine, however, the magnitude is desired not to exceed 100 $\mu$A. The time required for the electrolysis is variable with the potential for the electrolysis. Generally, about one hour's electrolysis suffices. It is permissible to continue the electrolysis for a few days.

The bath temperature is not subject to any particular restriction except for the requirement that it should not exceed the boiling point of the solvent to be used and should exceed the solidifying point thereof. It generally falls in the range of 0° to 30° C.

In the method of this invention, when the electrolysis is carried out under the conditions mentioned above, cyanometallophthalocyanine crystals are deposited on the anode or in the electrolyte. These crystals have a blackish purple metallic luster and are in the shape of needles or parallelepipedons. They are insoluble in ordinary solvents. Depending on the conditions of the electrolysis, these crystals can occur in varying lengths and widths, ranging from 1 mm to several mm. The crystals of a particularly large size can be produced by using a point electrode (not more than 0.2 cm$^2$ in area) of platinum, holding an anode at a potential of about 1.0 V relative to a silver-silver chloride reference electrode, and carrying out electrolysis with a feeble current for several days. In this case, the crystals are obtained in a length of about 1 cm.

These crystals are identified by elementary analysis and IR measurement to be composed of cyanometallophthalocyanine.

When the crystals of cyanometallophthalocyanine obtained by this invention have a very small size, they can be molded in the form of pellets without difficulty. When they are obtained in a large size, they can be tested in their unaltered form for electroconductivity by the two-probe method or the four-probe method. They are organic electroconductive crystals having high electroconductivity ranging from the orders of $10^{-4}$ to $10^1$ S/cm, though variable with the particular type of core metal.

The crystals of cyanometallophthalocyanine, when necessary, may incorporate therein at least one doping substance selected from the group consisting of electron accepting compounds such as, for example, iodine, bromine, arsenic pentafluoride, and sulfur trioxide and electron donating compounds such as, for example, lithium, sodium, and potassium by exposing the crystals to the vapor of the doping substance or impregnating the crystals with the doping substance. The amount of the doping substance to be incorporated in the crystals is in the range of 5 mol % to 30 mol % based on the amount of the crystals.

In consequence of the addition of the doping substance, there are obtained organic electroconductive crystals, possessing high electroconductivity rising in the range of $10^{-2}$ to $10^2$ S/cm.

By the method of this invention, organic electroconductive crystals excelling in stability, moldability, and ease of mechanical handling and exhibiting high electroconductivity can be produced with ease. To be specific, the organic electroconductive crystals obtained by the method of this invention are characterized by exhibiting high electroconductivity over in a wide range of temperatures, enjoying stability in the air, and permitting ease of mechanical handling. Owing to these features, they make a suitable material for various electronic parts, electrodes, and sensors.

Now, this invention will be described more specifically below with reference to a referential experiment and working examples.

Referential Experiment: Production of potassium salt of dicyanocobalt(III)phthalocyanine Into 250 ml of nitrobenzene, 7 g of cobalt(II)phthalocyanine and 70 ml of thionyl chloride were added. The resultant mixture was stirred at 60° C. for four hours, cooled and then filtered to obtain brown dichlorocobalt(III)phthalocyanine.

Into 300 ml of ethanol, 6 g of dichlorocobalt(III)phthalocyanine and 2.4 g of potassium cyanide were added. The resultant mixture was stirred and refluxed for reaction at 96 hours. After completion of the reaction, the reaction product was filtered to separate the precipitate. The separated precipitate was extracted with acetone by a Soxhlet extractor. The acetone extract was evaporated under reduced pressure to expel the acetone and obtain 3.7 g of a purple powder of potassium salt of dicyanocobalt(III)phthalocyanine.

The physical constants of the potassium salt are shown below.

| | Elementary analyses (%) | | | |
|---|---|---|---|---|
| | Hydrogen | Carbon | Nitrogen | Cobalt |
| Found | 3.2 | 57.0 | 18.9 | 8.0 |
| Calculated | 3.4 | 54.2 | 18.6 | 7.8 |
| (as pentahydrate of potassium salt of dicyanocobalt(III)phthalocyanine) | | | | |

Electroconductivity: $1 \times 10^{-7}$ S/cm

EXAMPLE 1

In 40 ml of acetonitrile, 240 mg of the potassium salt of dicyanocobalt(III)phthalocyanine obtained in Referential Experiment was dissolved. In an electrolytic cell provided, as illustrated in FIG. 1, with a tripolar type electrode, i.e. a point electrode (1) (0.2 cm² in surface area) of platinum, a silver-silver chloride reference electrode (2), and another point electrode (3) of platinum, the solution (4) prepared as an electrolyte as described above was electrolyzed for 24 hours, with the anode kept at +1.3 V. As a result, blackish purple crystals shown in FIG. 2 as (5) were deposited on the anode. The crystals were in the shape of parallelepipedal plates 6 mm in major side, 2 mm in minor side, and 0.5 mm in thickness. They were not soluble in ordinary solvents. By elementary analysis, these crystals were confirmed to be composed of cyanocobalt(III)phthalocyanine.

| | Elementary analyses (%) | | | |
|---|---|---|---|---|
| | Hydrogen | Carbon | Nitrogen | Cobalt |
| Found | 2.7 | 66.4 | 21.2 | 9.7 |
| Calculated | 2.70 | 66.34 | 21.10 | 9.86 |

Since these crystals were amply large, they were tested in their unaltered form for electroconductivity by the four-probe method. In an atmosphere of argon, the electroconductivity at room temperature was found to be 60 S/cm. The activating energy for electroconductivity at room temperature was found to be 0.04 eV. When the crystals were exposed to the vapor of iodine, they were doped with iodine. Consequently, their electroconductivity was increased to about 100 S/cm.

EXAMPLE 2

In 40 ml of acetone, 120 mg of sodium salt of dicyanocobalt(III)phthalocyanine synthetized by following the procedure of Referential Example was dissolved. In an electrolytic cell provided, as illustrated in FIG. 3, with bipolar type electrodes, i.e. two platinum plates (6), (7) (4 cm² in surface area), the solution (8) prepared as an electrolyte as described above was electrolyzed for three hours and the potential between the electrodes at 3 V. After completion of the electrolysis, countless fine crystals of a blackish purple metallic luster were found to have been deposited on the platinum anodes. An average shape of them was illustrated in FIG. 4 as (9). By elementary analysis, these crystals were found to be composed of cyanocobalt(III)phthalocyanine similarly to the crystals of Example 1.

The crystals were molded with a compression molding device in the form of pellets and tested for electroconductivity by the two-probe method. The electroconductivity at room temperature was found to re $5 \times 10^{-2}$ S/cm.

When these pellets were exposed to the vapor of sulfur trioxide, their electroconductivity was increased up to $8 \times 10^{-1}$ S/cm.

EXAMPLE 3

In 100 ml of acetonitrile, 300 mg of sodium salt of dicyanoiron(III)phthalocyanine synthesized by following the procedure of Referential Experiment was dissolved. In an electrolytic cell provided, similarly to the electrode of FIG. 1, with tripolar type electrodes, i.e. two platinum plates 1 cm² in surface area and one silver-silver chloride reference electrode, the solution prepared as an electrolyte as described above was electrolyzed for 24 hours, with the anode kept at +1.5 V relative to the reference electrode. Consequently, blackish purple crystals were deposited on the anodes and in the solution. The crystals, by photography with a scanning electron microscope, were found to be in the form of needles 5 to 1 mm in length. By elementary analysis, these crystals were confirmed to be composed of cyanoiron(III)phthalocyanine.

| | Elementary analyses (%) | | | |
|---|---|---|---|---|
| | Hydrogen | Carbon | Nitrogen | Iron |
| Found | 2.6 | 66.8 | 21.3 | 9.3 |
| Calculated | 2.69 | 66.69 | 21.22 | 9.40 |

The crystals measuring about 5 mm in length were selected from the crystals obtained in this example and tested for electroconductivity by the two-probe method. The electroconductivity at room temperature in the air was found to be 6 S/cm.

EXAMPLE 4

In 50 ml of dimethylacetamide, 100 mg of sodium salt of dicyanoiron(III)phthalocyanine was dissolved. In an electrolytic cell provided, similarly to the electrolytic cell of FIG. 3, with bipolar type electrodes, i.e. two platinum plates 4 cm² in surface area, the solution prepared as an electrolyte as described above was electrolyzed for 10 hours, with the potential between the two electrodes kept at 3 V. After completion of the electrolysis, countless fine blackish purple crystals were found deposited on the anodes. The crystals were not soluble in ordinary solvents. By elementary analysis, the crystals were confirmed to be composed of the same cyanoiron(III)phthalocyanine as the crystals of Example 3.

The crystals were molded in the form of pellets with a compression molding device and tested for electroconductivity by the two-probe method. The electroconductivity at room temperature was found to be $1 \times 10^{-3}$ S/cm.

When the pellets were immersed in a solution of lithium naphthalide in tetrahydrofuran to be doped with lithium, their electroconductivity was increased to $5 \times 10^{-2}$ S/cm.

EXAMPLE 5

In 40 ml of acetone, 120 mg of potassium salt of dicyanomanganese(III)phthalocyanine synthetized by following the procedure of Reference Experiment was dissolved. When the solution was electrolyzed under the same conditions as those of Example 1, crystals of the form of flat plates having a metallic luster were found deposited on the anodes and in the solution. The crystals were 2 to 3 mm in size. By elementary analysis, they were conformed to be composed of cyanomanganese(III)-phthalocyanine.

| | Elementary analyses (%) | | | |
|---|---|---|---|---|
| | Hydrogen | Carbon | Nitrogen | Manganese |
| Found | 2.7 | 66.8 | 21.3 | 9.2 |
| Calculated | 2.70 | 66.79 | 21.25 | 9.26 |

The crystals in their unaltered form were tested for electroconductivity by the two-probe method. The electroconductivity at room temperature was found to be $3 \times 10^{-3}$ S/cm.

What is claimed is:

1. A method for the production of organic electroconductive crystals, characterized by the steps of preparing a solution containing an alkali salt of dicyanometallophthalocyanine as an electrolyte and electrolyzing said electrolyte thereby causing deposition of cyanometallophthalocyanine crystals.

2. A method according to claim 1, wherein said alkali salt of dicyanometallophthalocyanine is at least one member selected from the group consisting of potassium salt of dicyanocobalt(III)phthalocyanine, sodium salt of dicyanocobalt(III)phthalocyanine, potassium salt of dicyanomanganese(III)phthalocyanine, sodium salt of dicyanomanganese(III)phthalocyanine, potassium salt of dicyanoiron(III)phthalocyanine, and sodium salt of dicyanoiron(III)phthalocyanine.

3. A method according to claim 1, wherein the concentration of said alkali salt of dicyanometallophthalocyanine in said electrolyte is in the range of 0.1 to 100 m.mols/liter.

4. A method for the production of organic electroconductive crystals, characterized by the steps of preparing a solution containing an alkali salt of dicyanometallophthalocyanine as an electrolyte, electrolyzing said electrolyte thereby causing deposition of cyanometallophthalocyanine crystals, and subsequently doping said cyanometallophthalocyanine crystals with at least one substance selected from the group consisting of electron accepting compounds and electron donating compounds.

5. A method according to claim 4, wherein said alkali salt of dicyanometallophthalocyanine is at least one member selected from the group consisting of potassium salt of dicyanocobalt(III)phthalocyanine, sodium salt of dicyanocobalt(III)phthalocyanine, potassium salt of dicyanomanganese(III)phthalocyanine, sodium salt of dicyanomanganese(III)phthalocyanine, potassium salt of dicyanoiron(III)phthalocyanine, and sodium salt of dicyanoiron(III)phthalocyanine.

6. A method according to claim 4, wherein the concentration of said alkali salt of dicyanometallophthalocyanine in said electrolyte is in the range of 0.1 to 100 m.mols/liter.

* * * * *